US005489513A

United States Patent [19]
Springer et al.

[11] Patent Number: 5,489,513
[45] Date of Patent: Feb. 6, 1996

[54] **SPECIFIC GENE PROBES AND PROCESSES FOR THE DIAGNOSTIC INVESTIGATION OF *CANDIDA ALBICANS***

[75] Inventors: Wolfgang Springer, Wuppertal; Manfred Plempel, Haan; Antonius Löbberding, Wuppertal, all of Germany

[73] Assignee: Bayer Akteingesellschaft, Leverkusen, Germany

[21] Appl. No.: 145,705

[22] Filed: Oct. 28, 1993

[30] Foreign Application Priority Data

Oct. 30, 1992 [DE] Germany .................... 42 36 708.5

[51] Int. Cl.⁶ ................... C12Q 1/68; C07H 21/04; C12P 19/34
[52] U.S. Cl. ............ 435/6; 435/91.2; 536/24.32; 536/24.33; 935/8; 935/77; 935/78
[58] Field of Search .............. 435/6, 91.2, 91.52, 435/91.31; 536/24.3, 34.32, 34.33; 935/77, 78, 16, 17, 5, 8

[56] References Cited

U.S. PATENT DOCUMENTS 5,332,660 7/1994 Takeda ......................... 435/6

FOREIGN PATENT DOCUMENTS

| | | |
|---|---|---|
| 0200362 | 12/1986 | European Pat. Off. . |
| 0329822 | 8/1989 | European Pat. Off. . |
| 0427074 | 5/1991 | European Pat. Off. . |
| 0468812 | 1/1992 | European Pat. Off. . |
| 0422872 | 4/1994 | European Pat. Off. . |
| 0320308 | 6/1994 | European Pat. Off. . |
| 87/06270 | 10/1987 | WIPO . |

OTHER PUBLICATIONS

Anderson et al J. Clin Microbiol (Jun. 1993) 31: 1472–1480.
Lasker et al, Gene (Jul. 1992) 116: 51–57.
Oren et al, Nucleic Acid Research (1991) 19: 7113–7116.
Myawa et al J. Clin Microb (Apr. 1992) 30: 894–900.
N. Dattagupta, et al., Analytical Biochem. 177, 85, 1989.
Rigby, P. W. et al, J. Mol. Biol. 113, 237, 1977.
Feinberg und Vogelstein, Anal. Biochem. 132, 6, 1983.
M. M. Mason et al., J. Clin. Microbiol. 25, 563, 1987.
Maniatis et al, Molecular cloning, Cold Spring Harbor Laboratory Press, 1989.
Southern, J. Mol. Biol. 98, 503, 1978.
Sanger et al., PNAS, 74, 5463 (1977).
Henikoff S., Gene, 73, 351, 1984.
Tetrahedron Letters 22, 1859, 1981, Beaucage et al.
Chang, L. M. S., Bollum T. J., J. Biol, Chem. 246, 909, 1971.
Journal of Bacteriology, vol. 173, No. 2, Jan. 1991, pp. 842–850, Sadhu et al.
Journal of Clinical Microbiology, vol. 26, No. 9, Sep. 1988, pp. 1720–1724, Cutler et al.
Diagn. Microbiol. Infect. Dis., vol. 10, No. 3, 1988, pp. 171–179, Cheung et al.

*Primary Examiner*—Gary Jones
*Assistant Examiner*—Carla Myers
*Attorney, Agent, or Firm*—Sprung Horn Kramer & Woods

[57] ABSTRACT

Polynucleotide and oligonucleotide probes are described for the diagnostic investigation of mycoses which are caused by *Candida albicans*. These gene probes are complementary to parts of the genome of *C. albicans* and are suitable for identifying *C. albicans* nucleic acids in any sample material, even that which has been amplified. They do not hybridise with nucleic acids from other fungi, bacteria, animals or plants. Processes are described for the diagnosis of *C. albicans* in clinical samples as well.

22 Claims, 6 Drawing Sheets

Additional cleavage sites: Sau 3a, Xba I, Ava I, Dra I, Dde I, Taq I, Hae III, Hha I, Hpa I

Additional cleavage sites: AvaI, DraI, DdeI, AccI, HaeIII, Sau 3a, EcoRV, XbaI, NcoI, SacI, TaqI Additional cleavage sites: Sau 3a, Xba I, Ava I, Dra I, Dde I, Taq I, Hae III, Hha I, Hpa I Additional cleavage sites: Sau 3a, EcoRV, NcoI, AvaI, DraI, DdeI, TaqI, HaeIII Additional cleavage sites: AvaI, DraI, DdeI, HaeIII, Sau 3a, SspI, BglII, EcoRV, NcoI, TaqI Additional cleavage sites: Sau 3a, EcoRV, DraI, DdeI, TaqI, SacI, HaeIII, SspI Additional cleavage sites: Hae III, Sau 3a, AvaI, SspI, DdeI, NcoI, TaqI

SPECIFIC GENE PROBES AND PROCESSES FOR THE DIAGNOSTIC INVESTIGATION OF *CANDIDA ALBICANS*

Candida is a ubiquitous yeast which is known as the causative agent of candidiasis (Candida mycosis). At least 90% of the disorders are caused by the species *Candida albicans*.

*C. albicans* is an opportunistic yeast which is only able to elicit mild skin infections in normal individuals. Fungal infections associated with severe infections of the mucous membrane and with invasive infections of individual organs are observed ever more frequently as a result of the increasing number of patients with immune defence weakness, e.g. AIDS patients or patients undergoing immunosuppressive therapy.

If left untreated, such systemic infections frequently lead to the death of the patients. At present, the therapy which is in principle available for invasive infections is based on relatively few antimycotics, such as amphotericin B and flucytosine, or the azole derivatives fluconazole and itraconazole.

These antimycotics cause serious, sometimes different, side effects, such as renal insufficiency, hypocalcaemia and anaemia, as well as unpleasant constitutional symptoms such as fever, shivering and low blood pressure.

For this reason, doctors and clinicians are interested, for achieving direct and effective therapy, in having available diagnostic procedures which permit the earliest possible identification of the fungal pathogens.

Conventional methods of diagnosis are based on the in-vitro cultivation of the pathogens and the identification of the fungal species by means of morphological, physiological and biochemical methods. The culturing of *Candida albicans* from blood is frequently very difficult and unreliable.

The gene-probe method, in particular in association with amplification techniques, is a method which is rapid, specific and highly sensitive, and which permits early identification of the pathogens at the DNA/RNA level. The technique can be carried out directly on the material to be investigated without in-vitro cultivation.

DNA diagnostics is based on DNA/RNA hybridisation technology, i.e. the specific in-vitro binding of complementary single-strand nucleic acid with the formation of Watson-Crick base pairs. The DNA/DNA or DNA/RNA double strands which are formed are also termed DNA hybrids. To detect the specific DNA or RNA of a pathogen by the hybridisation reaction, complementary, sequence-specific gene probes are used. These gene probes are either short, chemically synthesised, oligonucleotide probes of a length of 10 to 100 nucleotides, or else DNA/RNA fragments of 0.5 to 10 kb, which are prepared by recombinant gene technology.

The gene probes can be provided with a radioactive label either photochemically (N. Dattagupta et al., Analytical Biochem. 177,85, 1989), or enzymatically by nick translation (Rigby, P. W. et al., J. Mol. Biol. 113, 237, 1977) or random primed techniques (Feinberg and Vogelstein, Anal. Biochem. 132, 6, 1983). Labelling with $^{32}$P NTPs, or non-radioactive labelling with digoxigenin-dUTP or biotin-dUTP, or direct labelling with enzymes, such as alkaline phosphatase or horseradish peroxidase, are suitable for this purpose.

For the specific hybridisation between the nucleic acid, which is to be detected, of the pathogen and the pathogen-specific gene probe, the nucleic acids are first separated into single strands by denaturation (heat or alkali treatment) and then very specifically hybridised with each other under stringent conditions which are achieved by temperature, ionic strength of the buffer and organic solvents. Under appropriate hybridisation conditions, the gene probe only binds to complementary sequences of the DNA or RNA to be detected. This hybridisation reaction can be carried out in various experimental formats, e.g. as a solid-phase hybridisation of target DNA or gene probe which is coupled to a support, such as, e.g., nitrocellulose, or as a liquid hybridisation. The evaluation (read-out) is effected by way of the labelling of the gene probe with a reporter molecule as explained above. The hybridisation complex of target DNA and labelled gene probe is determined quantitatively, after removing unbound gene probe, by way of the reporter molecule employed. This read-out can be effected directly, in the case of fluorescence labelling or radioactive labelling, or indirectly by means of enzyme tests and immunological processes using antibody conjugates which contain enzymes such as alkaline phosphatase and then permit a colour reaction or a chemiluminescence reaction.

On the basis of the detection of single genes, the test sensitivity of this gene-probe diagnostic method is in the range of $10^5$ to $10^6$ organisms. The test sensitivity can be increased by combination with DNA or RNA amplification techniques, such as the PCR (EP 200 362), LCR (EP 320 308), NASBA (EP 329 822), Qβ (PCT 87/06270) or HAS (EP 427 074) techniques. Using these techniques, the DNA to be detected can be multiplied by a factor of up to $10^9$. The detection of individual DNA molecules thus becomes possible by combining amplification and hybridisation.

Since organism numbers of $10^2$ to $10^3$ organisms/ml occur in the blood in association with infections, this technology offers the possibility of early recognition of infections in progress.

Gene probes are described (EP 422 872, Genetrak Systems) which are based on the detection of ribosomal sequences and which are used for detecting fungi generally, in order to differentiate between bacterial, viral and fungal infections. Since, with current antimycotics, broad-spectrum therapy cannot be applied to all fungal disorders, it is particularly important to develop appropriate gene probes for the individual pathogens. In the present invention, novel, specific, and particularly sensitive, gene probes for *C. albicans* are described.

The novel gene probes were developed according to a process which provides specific, and particularly strong, hybridisation signals as a result of hybridisation with naturally occurring amplified sequences. The construction of oligonucleotide probes and polynucleotide probes for *C. albicans* on the basis of this process is described in the invention. The novel gene probes are not based on gene sequences for pathogenicity factors such as the aspartate protease (EP 468 812) or other structural genes (M. M. Mason et al., J. Clin. Microbiol., 25, 563, 1987) (I. Oren et al., Nucleic Acids Res., 19, 7113, 1991). GenBank and EMBL nucleotide sequence data bases were screened for homology with our gene-probe sequences. No homologies to known fungal or Candida gene probes were found.

With the gene probes described in the invention, it was established that the whole spectrum of *C. albicans* isolates can be detected by the combination of two particular oligonucleotide or polynucleotide probes.

In addition, a process for employing these gene probes in hybridisation tests is described, with which tests specific hybridisation to *C. albicans* target DNA is effected.

Furthermore, in this invention, the combination of these hybridisation processes with application techniques is described through which a very marked improvement of the test sensitivity is achieved.

The use of these gene probes and test processes for detecting C. albicans in clinical samples is also described.

Construction of specific gene probes for C. albicans

To develop specific gene probes for C. albicans which were to have a high test sensitivity, the following strategy was adopted:

1. Those gene regions should be selected as target sequences which are present in the genome in multiply amplified form.
2. The amplified sequences should be strongly conserved and not contain any deletions or insertions.
3. The amplified sequences should be specific for C. albicans, and not react with any other fungi or bacteria, or other eukaryotic cells.

To identify such gene probes, a gene bank of C. albicans was first prepared by the customary recombinant-DNA processes (Maniatis et al., Molecular cloning, Cold Spring Harbor Laboratory Press, 1989) in E. coli 5K. The recombinant clones were analysed by molecular biological techniques for the C. albicans DNA inserts incorporated in the plasmid vector pBR322. Clones having a C. albicans insert size of 0.5 to 7 kb were used for further analysis.

Using reversed-phase hybridisation, an examination was made of which DNA fragments yielded a particularly good hybridisation signal with C. albicans DNA and consequently were present in the genome in amplified form. To do this, the recombinant plasmids from the E. coli clones were separated by gel electrophoresis according to the Southern blot technique (Southern, J. Mol. Biol. 98, 503, 1978), transferred to nitrocellulose membranes and fixed, and then hybridised with C. albicans genomic DNA which had been labelled by random priming.

Recombinant clones whose C. albicans inserts exhibited particularly strong hybridisation signals were employed for the subsequent specificity analyses.

The specificity of the C. albicans gene fragments was examined by slot blot tests using a Minifold II filtration apparatus from Schleicher and Schell. DNA from various Candida strains and a series of Gram-positive and Gram-negative bacteria, DNA from other fungi, and various nucleic acids from eukaryotic cells, were applied to nitrocellulose membranes, and fixed. The selected C. albicans gene fragments were provided with non-radioactive reporter molecules using the random-primed technique and then hybridised with the slot blots. Those gene probes which only hybridised with the C. albicans DNA, and did not give a hybridisation signal with the other nucleic acid lysates, were selected.

Using 87 different clinical isolates of C. albicans, the detection spectrum of the selected specific gene probes was analysed by the slot blot technique. None of the isolated gene probes permitted simultaneous detection of all the strains. The gene probe 431-19, having the broadest detection spectrum for C. albicans, is depicted in FIG. 2. Using it, 95% of all clinical isolates are detected.

During the microbiological characterisation of the 4 C. albicans strains which were not detected, it was established, in physiological and biological tests, that these were atypical C. albicans strains. Gene banks were also prepared from these 4 strains, and specific gene probes constructed as in the above-described hybridisation tests.

Gene probes were obtained which, apart from the physiological atypical C. albicans strains, also detected various other C. albicans isolates, and gene probes which only detected the atypical isolates. A restriction map of the gene probe 436-1 is depicted in FIG. 5.

By combining gene probe 431-19 with gene probe 436-1 it was possible to detect the whole spectrum of C. albicans strains in one hybridisation test.

Molecular description of the polynucleotide probes

Specific polynucleotide probes for C. albicans were constructed according to the above-described process (FIGS. 1–6). The best results, with regard to specificity, test sensitivity and detection spectrum for C. albicans, were achieved with the gene probe 431-19. This gene probe was developed from a 7 kb gene probe 309-6 (FIG. 1) by subcloning. For this, the gene probe was first characterised according to molecular biological techniques by cleavage with restriction enzymes (FIG. 1). The individual gene fragments of gene probe 309-6 were subcloned into pBR322 plasmid vectors as ClaI-BamHI and ClaI-ClaI fragments, and their specificity was analysed in comparison with the starting probe. The above-described advantages were established for gene probe 431-19. A restriction map based on the restriction enzymes ClaI, BamHI, SalI, AccI and SphI is described in FIG. 2. Using the existing restriction map, the gene probe was sequenced by the method of Sanger in order to be able to prepare oligonucleotide probes for C. albicans based on the nucleotide sequence.

The gene probe 436-1, which is specific for the physiologically atypical strains, is described in FIG. 5. It was prepared from the 6.3 kb-sized gene probe 432-8 (FIG. 4) by subcloning using the restriction enzyme ClaI. The gene probe was also sequenced for synthesising oligonucleotide probes and for using amplification techniques.

The restriction maps of the gene probes 430-14 and 437-3 are described in FIGS. 3 and 6. Their hybridisation properties are evident from Table I.

Sequencing the polynucleotide probes

The sequencing of the described gene probes was carried out by the chain termination method of Sanger et al., PNAS, 74, 5463 (1977) using a Sequenase Kit from USB Biochemicals, Ohio, U.S.A. For the sequencing, the gene probes were recloned into the Bluescript vector pKS and deletion clones were then produced by the erase-a-base technology using a kit from Promega. This system is based on the method of Henikoff S, Gene, 73, 351, 1984, in which exonuclease III is used to digest DNA specifically from overlapping 5' ends or blunt ends. The uniform speed of the degradation by the enzyme makes possible the production of deletions at predetermined intervals by means of the time-dependent removal of aliquots from the reaction mixture. Using this technique, unidirectional deletions extending over several kbp can be constructed in this way within a few hours.

Molecular description of the oligonucleotide probes 23 100mer oligonucleotides from the polynucleotide probe 431.19 were prepared chemically by the phosphoramidite method of S. L. Beaucage and M. H. Caruthers, Tetrahedron Letters 22, 1859, 1981. The sequences of these oligonucleotide probes are described in the sequence listing, as is the complete nucleotide sequence of gene probe 431-19. The hybridisation properties of these oligonucleotide probes, in comparison to the polynucleotide probe 431-19, were tested on various nucleic acids from Candida isolates and Gram-positive and Gram-negative bacteria, as well as other fungi and eukaryotic cells (Table 3). Some differences in the strength of the hybridisation signals were observed in the different oligonucleotide probes. However, no significant differences between the individual gene probes were detected in relation to their specificity for *C. albicans*. It was not possible to observe any cross hybridisation with nucleic acids from other Candida species, fungi, or bacteria in any of the 23 oligonucleotide probes. All the 23 oligonucleotide probes are, therefore, suitable, in particular in combination with the oligonucleotide probes of the polynucleotide probe 436-1, for detecting *C. albicans*.

Oligonucleotide probes from the polynucleotide probe 436-1 were prepared chemically. The nucleotide sequences of the oligonucleotide probes are depicted in the sequence listing as SEQ ID NO: 25-38. The hybridisation properties of these oligonucleotide probes were examined, in comparison with the polynucleotide probe 436-1, on the four different nucleic acid lysates of the atypical *C. albicans* strains, as well as on Gram-positive and Gram-negative bacteria, fungi and eukaryotic cells. All 14 oligonucleotide probes examined are specific for the 4 unusual *C. albicans* strains, but do differ somewhat with regard to the strength of their hybridisation with the different Candida strains.

It was possible to combine oligonucleotide probes of the polynucleotide probe 431-19 and the polynucleotide probe 436-1 as desired in order to detect all the *C. albicans* isolates in one hybridisation test.

Example 1

Detection of *C. albicans* by slot blot hybridisation using the polynucleotide probe SPN 431.19

For the slot blot hybridisation, the nucleic acid from the sample material was isolated by means of analytical or preparative nucleic acid processes known per se, and then fixed on membranes, such as nitrocellulose or nylon, which are commercially available in various formats. The nucleic acid can be applied to the membranes using a filtration apparatus (e.g. Schleicher and Schüll Minifold II), and fixed, and then tested for hybridisation, under appropriate stringency conditions, with gene probes which are provided with reporter molecules. The greater the complementarity of the nucleotide sequences of target DNA and gene-probe DNA, the better is the hybridisation signal. The read-out of the slot blots or dot blots is effected in each case according to the labelling of the gene probe, e.g. by autoradiography ($^{32}$P), colour signal (alk. phosphatase, bromochloroindolyl phosphate/nitro blue tetrazolium), or chemiluminescence or fluorescence.

Isolation of Candida nucleic acid

The Candida strains cultured in the YM medium (Bacto yeast extract 4 g; Bacto malt extract 10 g; Bacto dextrose 4 g; H$_2$O 1 l, pH 7.3) were centrifuged down at 5000 rpm for 5 minutes and washed 2 times with 1M sorbitol.

The cells were re-suspended in 1 ml of sorbitol containing 100 μg of Zymolase-100T from Arthrobacter luteus (10,000 units/g), and incubated at 37° C. for about 30 minutes.

Subsequently, 200 μl of EDTA, 0.5M, pH 8.0, and 200 μl of 10% strength lauroyl sarcosine were added to the samples, which were then heated for 3 minutes at 100° C. in a water bath. After cooling in ice/isopropanol, the samples were made up to 20 ml with 1×TE (10 mM Tris/HCl, pH 8, 1 mM EDTA), and treated 2× with Tris-saturated phenol;

they were then centrifuged at 6000 rpm, and the aqueous DNA phase was extracted 2× with ether in order to remove traces of phenol. After precipitating the DNA with isopropanol, and washing the DNA pellet with 70% ethanol, the samples were taken up in 1–2 ml of 1×TE and analysed by electrophoresis in a 0.8% strength agarose gel.

Isolation of bacterial nucleic acid 1.5 ml bacterial cultures or, in the case of preparative isolations, 10×1.5 ml of bacterial culture in Eppendorf batches, or 150 ml with correspondingly larger batches of buffer, were employed for dot blot hybridisations.

The method is described for 1.5 ml bacterial cultures. 1.5 ml bacterial cultures are centrifuged down at 6000 rpm. 500 μl of 15% strength sucrose in TE+2 mg/ml of lysozyme are added to the pellet. After incubating at 37° C. for 30 minutes, 50 ml of 0.5M EDTA, pH 8, is added, and if lysis is poor, the samples are treated at 65° C. for 10 minutes until complete lysis is achieved.

For further purification, 1 volume of phenol is added, and the sample is mixed well and then centrifuged at 10,000 rpm for 10 minutes. The upper, DNA-containing, phase is mixed with 100 μl of diethyl ether (Tris-saturated) and then centrifuged at 10,000 rpm for one minute. The upper ether phase is discarded. ⅒ volume of 3M sodium acetate and 1 volume of isopropanol are added to the lower DNA phase and the mixture is left to stand at room temperature for 5 minutes. Subsequently, centrifugation takes place at 10,000 rpm for 10 minutes, the supernatant is decanted and the pellet is dissolved in TE to half the original volume.

Isolation and labelling of the gene probe SPN 431.19

The polynucleotide probes were labelled by the random-primed method according to Feinberg and Vogelstein (Anal. Biochem. 132, 6, 1983) or by 3'end-group labelling using terminal transferase (Chang, L. M. S., Bollum T. J., J. Biol, Chem. 246, 909, 1971).

Performance of the slot blot hybridisation using gene probe SPN 431.19

The nucleic acid is brought to a volume of 200 μl with TE. Subsequently, the DNA is denatured at 100° C. for 10 minutes and the samples are then immediately placed in an ice/NaCl mixture. 200 μl of ice-cold 20×SSC are added and the samples are immediately applied to nitrocellulose/nylon filters using a Minifold II filtration apparatus from Schleicher and Schüll.

The filters had previously been pretreated for 10 minutes in distilled H$_2$O and then for 10 minutes in 10×SSC, and, after application of the DNA, were baked at 80° C. for 2 hours.

Solid-phase hybridisations using nitrocellulose or nylon membranes were carried out by the slot blot method.

The read-out was effected using anti-digoxigenin-antibody conjugates with alkaline phosphatase, and bromochloroindolyl phosphate/nitro blue tetrazolium, as the colour reaction, or with adamantane-dioxetane (AMPPD), as the chemiluminescence reaction.

For the hybridisation experiments, the DNA was first denatured into the DNA single strands by heating to 100° C. for 10 minutes and rapid cooling on ice/NaCl. Nitrocellulose membranes were pretreated by soaking in water and 20×SSC (NaCl, 3 mol/l, sodium citrate, 0.3 mol/l, pH 7) and subsequently dried. Nylon membranes were employed without pretreatment. The denatured nucleic acid extracts were applied to the nitrocellulose or nylon membranes using a filtration apparatus and subsequently fixed by being baked at 80° C. for 1 hour in vacuo or by 5 minutes of UV crosslinking using a UV transilluminator (nylon membrane). The nylon/nitrocellulose filters were sealed in a plastic bag together with 20 ml of hybridisation solution (5×SSC; blocking reagent, 0.5%, N-lauroyl sarcosine Na salt, 0.1%, SDS, 0.02%) and prehybridised at 68° C. for 1 hour. The prehybridisation solution was then replaced by 20 ml of hybridisation solution (same composition) which contained freshly denatured gene-probe DNA (100 ng). The hybridisation mixture was incubated at 68° C. for 2 hours. The filters were subsequently washed 2×5 minutes with 50 ml of 2×SSC, SDS, 0.1%, on each occasion at room temperature, and then once again 2×15 minutes with 0.1×SSC, 0.1% SDS, at 68° C. The filters were either used directly for the detection of the hybridised DNA, or stored air-dried for detection at a later stage.

Detection of the hybridised DNA

To detect the hybridised *C. albicans* DNA quantitatively, an immunological detection reaction was carried out. For this, a conjugate consisting of antibody coupled to alkaline phosphatase was used, which conjugate binds to the hybridised digoxigenin-labelled DNA. The colour reaction was evaluated quantitatively after 2 to 12 hours, using a Shimadzu CS-430 densitometer, by the addition, at alkaline pH, of the colourless 5-bromo- 4-chloro-3-indolyl phosphate and nitro blue tetrazolium.

The following buffers were employed for the detection reaction:

Buffer 1: Tris/HCl, 100 mmol/l, pH 7.5

Buffer 2: Blocking reagent, dissolve to 0.5% in buffer 1

Buffer 3: Tris/HCl, 100 mmol/l, $MgCl_2$, 50 mmol/l, pH 9.5

Buffer 4: Tris/HCl, 10 mmol/l, EDTA, 1 mmol/l, pH 8

Colour solution (freshly prepared): 45 µl of NBT and 35 µl of X-phosphate were added to 10 ml of buffer 3.

The nitrocellulose/nylon filters were washed for 1 min in buffer 1, and then incubated for 30 min with 100 µl of buffer 2, and washed once again with buffer 1. The antibody conjugate was diluted 1:5000 in buffer 1 and the filters were incubated for 30 min with about 20 µl of the diluted antibody conjugate solution. Unbound antibody conjugate was removed by washing 2×15 min with 100 µl of buffer 1, and the filters were subsequently equilibrated for 2 min with 20 µl of buffer 3. The filters were then incubated with 20 ml of colour solution in a sealed plastic bag in the dark. The colour intensity of the individual slot blots was determined densitometrically in comparison to a standard with applied *C. albicans* DNA.

Specificity of the *C. albicans* gene probe 431-19

The hybridisation properties of gene probe 431-19 with nucleic acids from various Candida strains and Gram-negative and Gram-positive bacteria, and various other fungi and eukaryotic cells, using the above hybridisation test, are summarised in Table 1. The hybridisation data demonstrate that the gene probe is absolutely specific for *Candida albicans*. Other nucleic acids are not detected by this gene probe.

Detection spectrum of gene probe 431.19 for *C. albicans* isolates

The hybridisation properties of gene probe 431.19 with nucleic acids from 87 *C. albicans* isolates are summarised in Table 2. The hybridisation data demonstrate that, while the gene probe hybridises with 84 *C. albicans* strains, 4 isolates are not detected. It is evident from physiological and biochemical tests that these 4 strains are not typical *C. albicans* isolates. However, these tests do confirm the affiliation of the strains to *C. albicans*.

Example 2

Detection of *C. albicans* by slot blot hybridisation using gene probe 436.1

Isolation of the nucleic acids from the different test samples, the isolation and labelling of the gene probe and the slot blot hybridisation were carried out as in Example 1.

Specificity of the *C. albicans* gene probe 436.1

The hybridisation properties of gene probe 436.1 with nucleic acids from various Candida strains and Gram-positive and Gram-negative bacteria, and various other fungi and eukaryotic cells, using the slot blot test described in Example 1, are summarised in Table 1. The hybridisation data demonstrate that the gene probe is specific for the 4 atypical Candida strains, while other Candida albicans strains, or other Candida species and other bacteria, fungi and eukaryotic cells are not detected.

Detection spectrum of gene probe 436.1 for *C. albicans* isolates

The hybridisation properties of gene probe 436.1 with nucleic acids from 87 *C. albicans* isolates are summarised in Table 2. The hybridisation data demonstrate that while the gene probe hybridises with the 4 rare *C. albicans* strains, the other 84 *C. albicans* strains are not detected.

Example 3

Detection of *C. albicans* by slot blot hybridisation using the gene-probe combination 431.19 and 436.1

The isolation of the nucleic acid from the sample material, the isolation and labelling of the gene probes, and the slot blot hybridisation were carried out as in Examples 1 and 2. 100 ng of each of the two gene probes were employed for the hybridisation experiment.

Specificity of the gene-probe combination 431.19 and 436.1

The hybridisation properties of the combined gene probes 431.19 and 436.1 with nucleic acids from various Candida isolates and Gram-negative and Gram-positive bacteria, and other fungi and eukaryotic cells, using the slot blot test, are summarised in Table 1.

The hybridisation data demonstrate that, using the gene-probe combination, *C. albicans* strains are detected specifically, and no hybridisation takes place with other Candida species or other fungi and bacteria.

Detection spectrum of the combined gene probes
431.19 and 436.1 for *C. albicans* isolates The hybridisation properties of the combined gene probes 431.19 and 436.1 with nucleic acids from 87 *C. albicans* isolates are summarised in Table 2. The hybridisation data demonstrate that the combined gene probes hybridise with all 87 *C. albicans* strains.

Example 4

Detection of *C. albicans* by slot blot hybridisation using oligonucleotide probes The sequences of the oligonucleotide probes based on the polynucleotide probe 431.19 (SEQ ID NO: 2-24) and the oligonucleotide probes based on the polynucleotide probe 436.1 (SEQ ID NO: 25-38) are depicted in the sequence listing. These oligonucleotide probes were synthesised by the phosphoramidite method of C. L. Beaucage and M. H. Caruthers, Tetrahedron Letters 22, 1859 (1981).

The oligonucleotide probes were labelled with a 3' or 5' end-group labelling kit from Boehringer, Mannheim, using terminal transferase or polynucleotide kinase. Alpha $^{32}$PdCTP or gamma $^{32}$PATP or non-radioactive dUTP-digoxigenin were employed as the reporter molecule for the 3' end-labelling.

The slot blot hybridisation was carried out as in Example 1. The hybridisation of the oligonucleotide probes 2-6 and 25-27 with nucleic acids from various Candida species and Gram-positive and Gram-negative bacteria, and other fungi and eukaryotic cells, is recorded in Table 3 by way of example for all the oligonucleotide probes tested.

The hybridisation data show that the oligonucleotide probes 2-6 listed in Table 3, as well as the oligonucleotide probes 7-24, which were also tested but which are not listed in the table, hybridise specifically with *C. albicans* and do not give any signal with any other Candida species or other bacteria and fungi. The only differences observed between the individual oligonucleotide probes were in hybridisation strength.

The hybridisation experiments were also carried out using shorter oligonucleotide probes (up to 15 mers), with the same hybridisation result.

The oligonucleotide probes 25-38 based on polynucleotide probe 436.1 only hybridised, like the polynucleotide probe, with the rare 4 *C. albicans* strains. By contrast, an arbitrary combination of oligonucleotide probes from the 431.19 series with oligonucleotide probes from the 436.1 series permitted the detection of all 87 *C. albicans* strains in one hybridisation experiment.

Example 5

Detection of amplified *C. albicans* DNA by liquid hybridisation using the combined gene probes 431.19 and 436.1

By combining the gene-probe technique with suitable target-amplification methods, such as PCR (EP 200 362), LCR (EP 320 308), NASBA (EP 329 822), Qβ (PCT 87/06270) or HAS (EP 427 074), a significant increase in sensitivity is achieved as compared with the conventional gene-probe read-out methods.

The amplification of the target DNA was carried out by the polymerase chain reaction and, alternatively, by the hairpin amplification method (HAS).

For the PCR reaction, 1 to 1000 pg of genomic DNA from *C. albicans*, 2 μmol of primer 1 (5'dTCGTCGATGG-TATCGTCGTTCTGC) (SEQ ID NO 39) or preferred primer 1' (5'dCCGAACCGCCATACCAGAAGCATT) (SEQ ID NO 40) and primer 2 (5'dCCGAACCGCGATACCAGAAG-CATT) (SEQ ID NO 41), 2.5 units of Taq polymerase from Cetus/Perkin-Elmer and 200 μmol of dNTPs and 6 μmol Digoxigenin-dUTP in each case were employed in a total of 100 μl of PCR buffer (50 mM KCl, 10 mM Tris/HCl, pH 8.3, 1.5 mM $MgCl_2$ and 0.01% gelatin). For amplification of the genomic DNA of a typical *C. albicans* strains (436.1 gene probe) additionally the primer 3 (5'dTTCTTACGAAT-GTTTGTGTT) (SEQ ID NO 42) or preferred primer 3' (5'dATCCACCAATATATATACACA) (SEQ ID NO 43) and primer 4 (5'dTTTGTCCTATTGGTACAGTT) (SEQ ID NO 44) were added. The amplification was carried out in a PCR processor from Cetus/Perkin-Elmer.

Using the samples, an initial melting of the DNA was carried out at 94° C. for 2 minutes 30 seconds, and then, in each cycle, the DNA was denatured at 94° C. for 1 minute, and the primer annealing was carried out at 40° to 45° C. for 2 minutes and the primer extension at 72° C. for 3 minutes. After 35 cycles, a final 20-minute extension was carried out at 72° C., and teh samples were then cooled at 4° C.

The liquid-hybridisation tests were carried out as reversed-phase tests using 100 ng of 5'-biotinylated gene probes and amplified *C. albicans* DNA in a volume of 50 μl.

After heating at 100° C. for 10 minutes, and subsequent cooling to 0° C., 50 μl of 2×Boehringer hybridisation mix were added and hybridisation was carried out at 68° C. for 1 hour. For separating the hybridisation complex 75 μl streptavidin coated magnetic particles from Dynal were used. The magnetic beads were pretreated with 1×Boehringer mix and, after separating them by means of a magnet, the liquid was pipetted off, and the hybridisation sample was added and incubated at room temperatue for ½ hour with gentle agitation. The coupled hybridisation complex was separated with the beads, the residual liquid was pipetted off, and washing then took place once with buffer A (2×SSC; 0.1% SDS) and then 2×with buffer B (0.1 SSC; 0.1% SDS).

Subsequently, the blocking reaction was carried out, and then the antibody reaction for detecting the hybridisation by means of chemiluminescence. The beads loaded with DNA were treated 1×with 150 μl of washing buffer (0.1M maleic acid, 0.1M NaCl, pH 5, 0.3% Tween 20) and then, after separating them and pipetting off the washing buffer, 400 μl of buffer 2 (0.1M maleic acid; 0.15M NaCl, pH 7.5; 1% blocking reagent (Boehringer)) were added. After incubating at room temperature for ½ hour, separation and pipetting off took place, and 100 μl of antibody conjugate solution (AC 1:10,000 in buffer 2) were added, and incubation took place at room temperature for ½ hour; separation and pipetting off then took place, followed by treatment with 400 μl of washing buffer for 2×15 minutes with gentle agitation. Subsequently, separation took place, followed by treatment with 150 μl of buffer 3 (0.1M Tris/HCl buffer containing 0.1M NaCl and 50mM $MgCl_2$, pH 9.5).

Separation then took place again, followed by incubation with 100 μl detection solution containing AMPPD 1:100 in buffer 3 in a water bath at 37° C. for 15 minutes; the chemiluminescence was then measured in a luminescence photometer at 477 nm (Lumac Lumacounter). Using this test, DNA quantities corresponding to $10^6$ to 10 *C. albicans* organisms can be detected. The same detection-limit of 10 organisms per ml of blood was also achieved following the addition of non-specific blood DNA. On its own, blood DNA only gives small background signals in the hybridisation test.

Example 6

Detection of a Candida mycosis in blood, sputum or biopsy material by amplification and hybridisation with the gene probes 431.19 and 436.1

The clinical sample material was homogenised and lysed by means of suitable mechanical or chemical methods of disruption, such as, e.g, using detergents such as SDS. When using blood as the starting material, the samples were lysed directly with sterile water, and the sedimented blood pellet containing the C. albicans organisms was then lysed by the enzymatic method of disruption described in Example 1. The C. albicans/blood lysate was then amplified with the aid of suitable amplification methods, as described in Example 5, using C. albicans-specific oligonucleotide primers. The amplified nucleic acid was then hybridised with the polynucleotide probes 431.19 and 436.1, and the specific hybridisation complex consisting of amplified C. albicans nucleic acid and gene-probe DNA, forming under stringent conditions, was separated using Dynal magnetic particles and determined quantitatively by chemiluminescence readout as in Example 5. The test can also be carried out with the oligonucleotide probes listed in the sequence listing.

C. albicans-specific hybridisation signals were still detected without difficulty at a concentration of 10 organisms in the blood lysates infected with C. albicans.

The gene probe originates from the strain C. albicans Hantschke.

Figure 1:
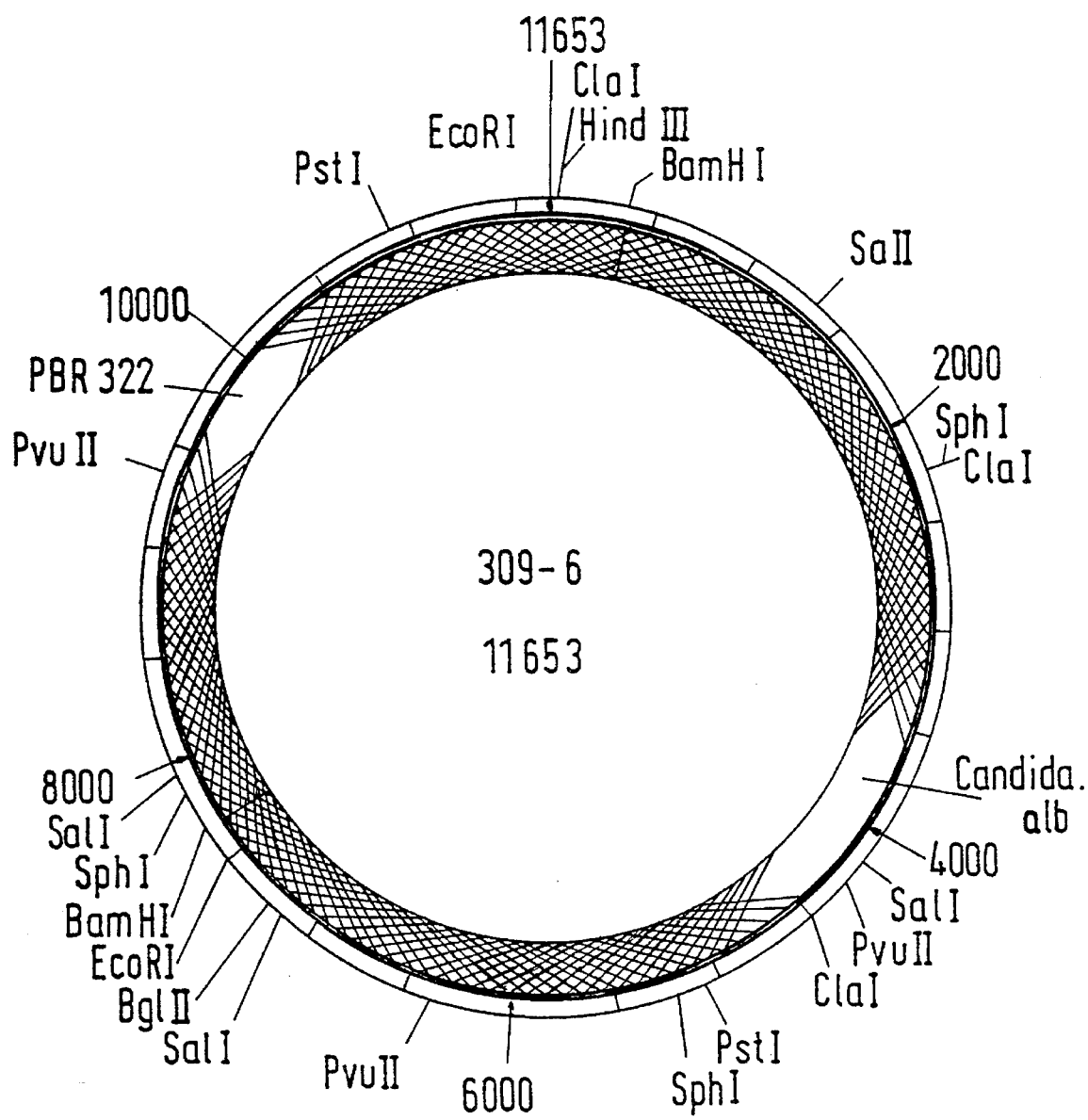
FIG. 1: Restriction map of the 7.2 kb BamHI gene-probe fragment 309-6 cloned into the plasmid vector pBR 322. Further restriction enzymes which do/do not cut the gene probe are listed in the text.
Figure 2:
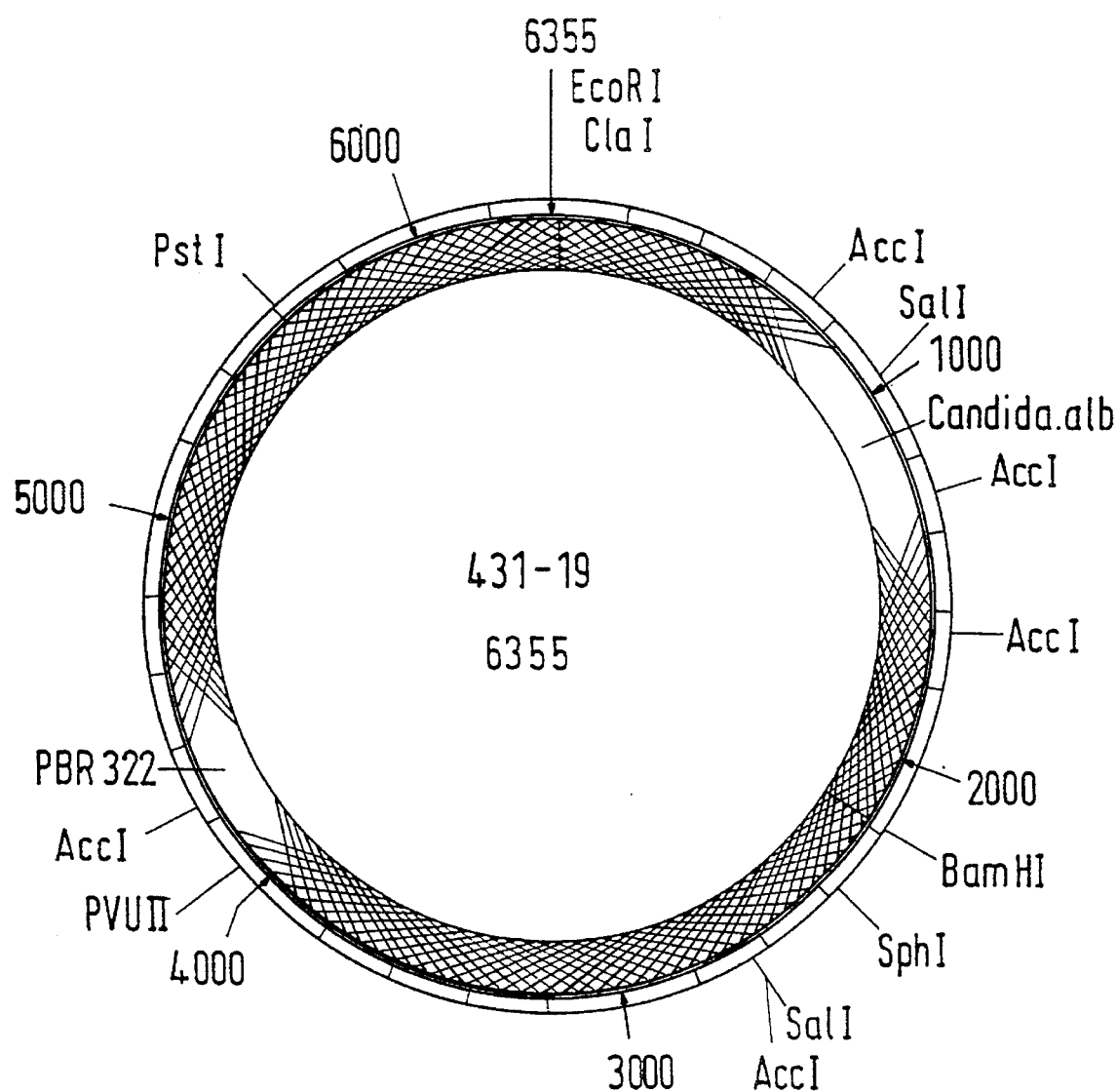

FIG. 2: Restriction map of the 2.2 kb ClaI-BamHI gene-probe fragment 431-19 cloned into the plasmid vector pBR 322. Further restriction enzymes which do/do not cut the gene probe are listed in the text.

The gene probe originates from the strain C. albicans Hantschke.

Figure 3:
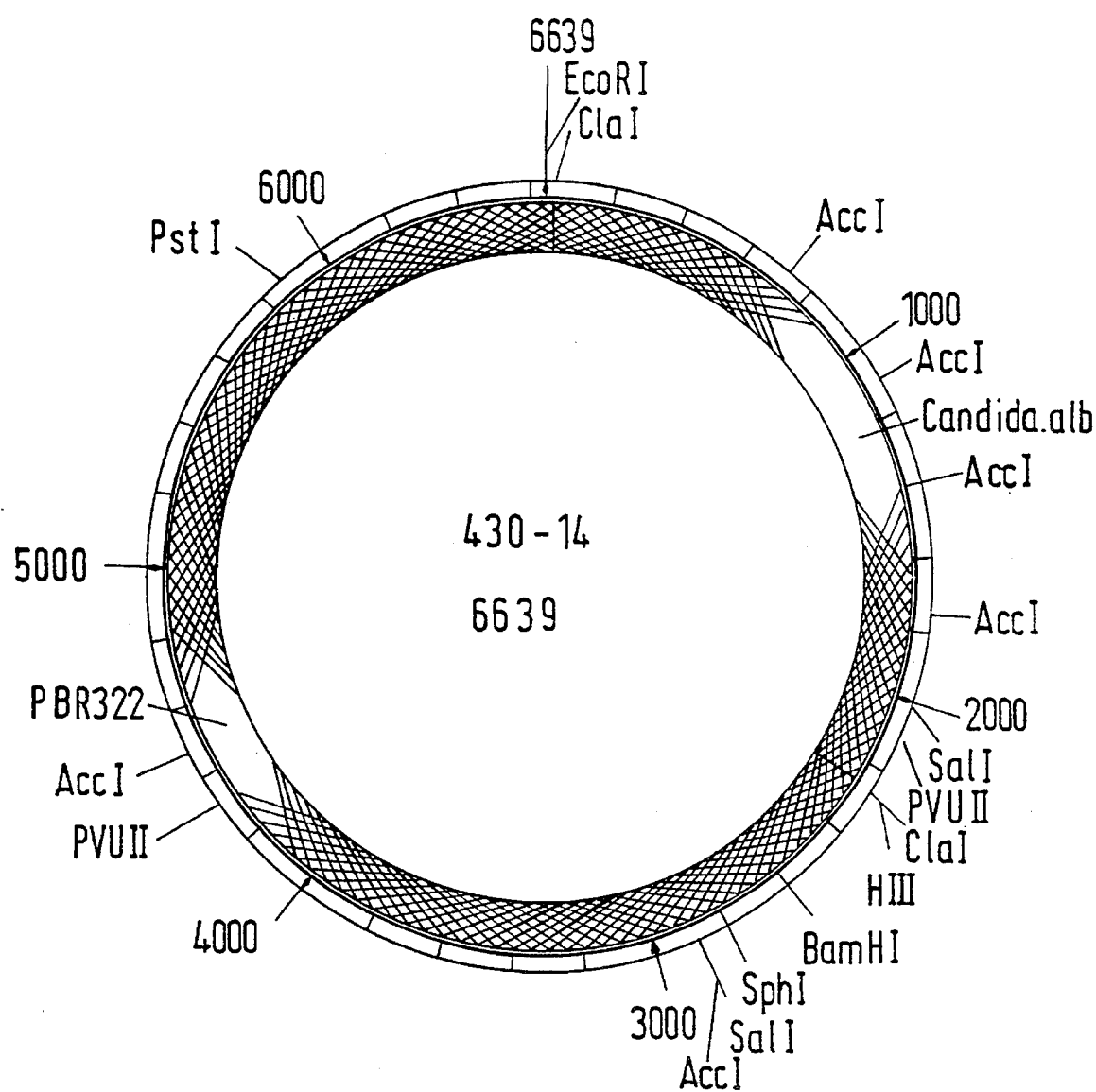

FIG. 3: Restriction map of the 2.3 kb ClaI-ClaI gene-probe fragment 430-14 cloned into the plasmid vector pBR 322. Further restriction enzymes which do/do not cut the gene probe are listed in the text.

The gene probe originates from the strain C. albicans Hantschke.

Figure 4:
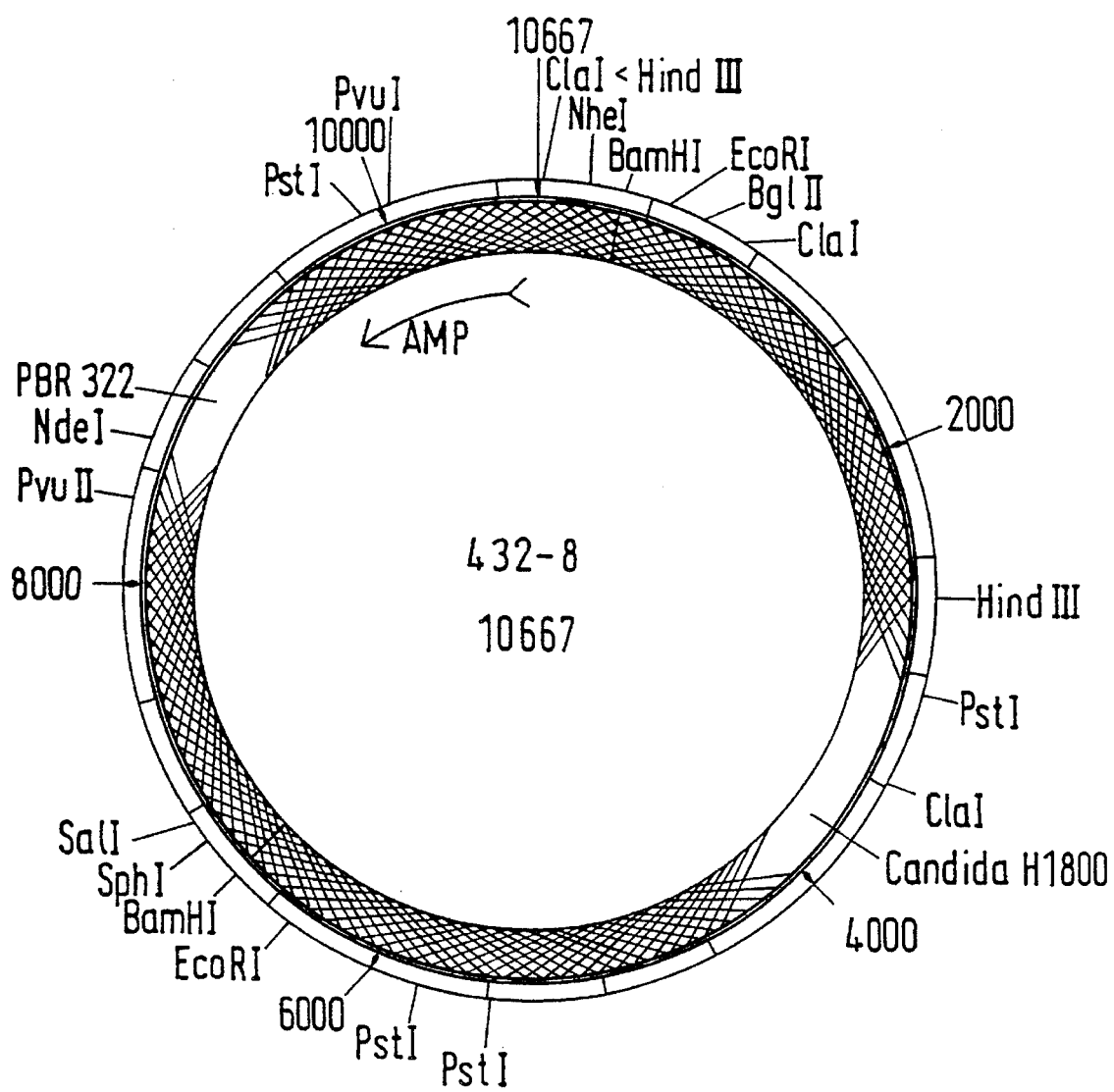

FIG. 4: Restriction map of the 6.3 kb BamHI gene-probe fragment 432-8 cloned into the plasmid vector pBR 322. Further restriction enzymes which do/do not cut the gene probe are listed in the text.

The gene probe originates from the strain C. albicans H 1800.

Figure 5:
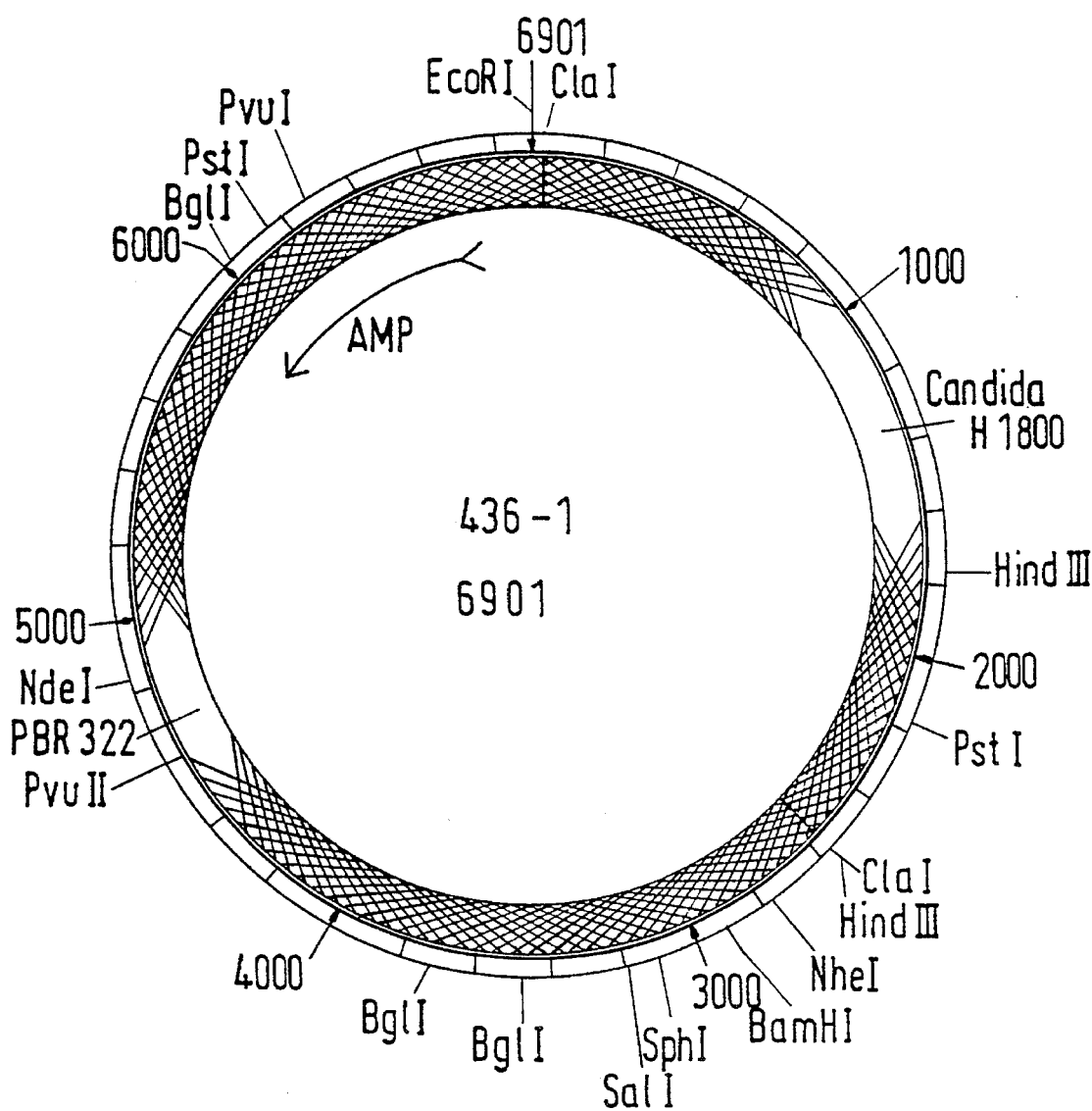

FIG. 5: Restriction map of the 2.6 kb ClaI gene-probe fragment 436-1 cloned into the plasmid vector pBR 322. Further restriction enzymes which do/do not cut the gene probe are listed in the text.

The gene probe originates from the strain C. albicans H 1800.

Figure 6:
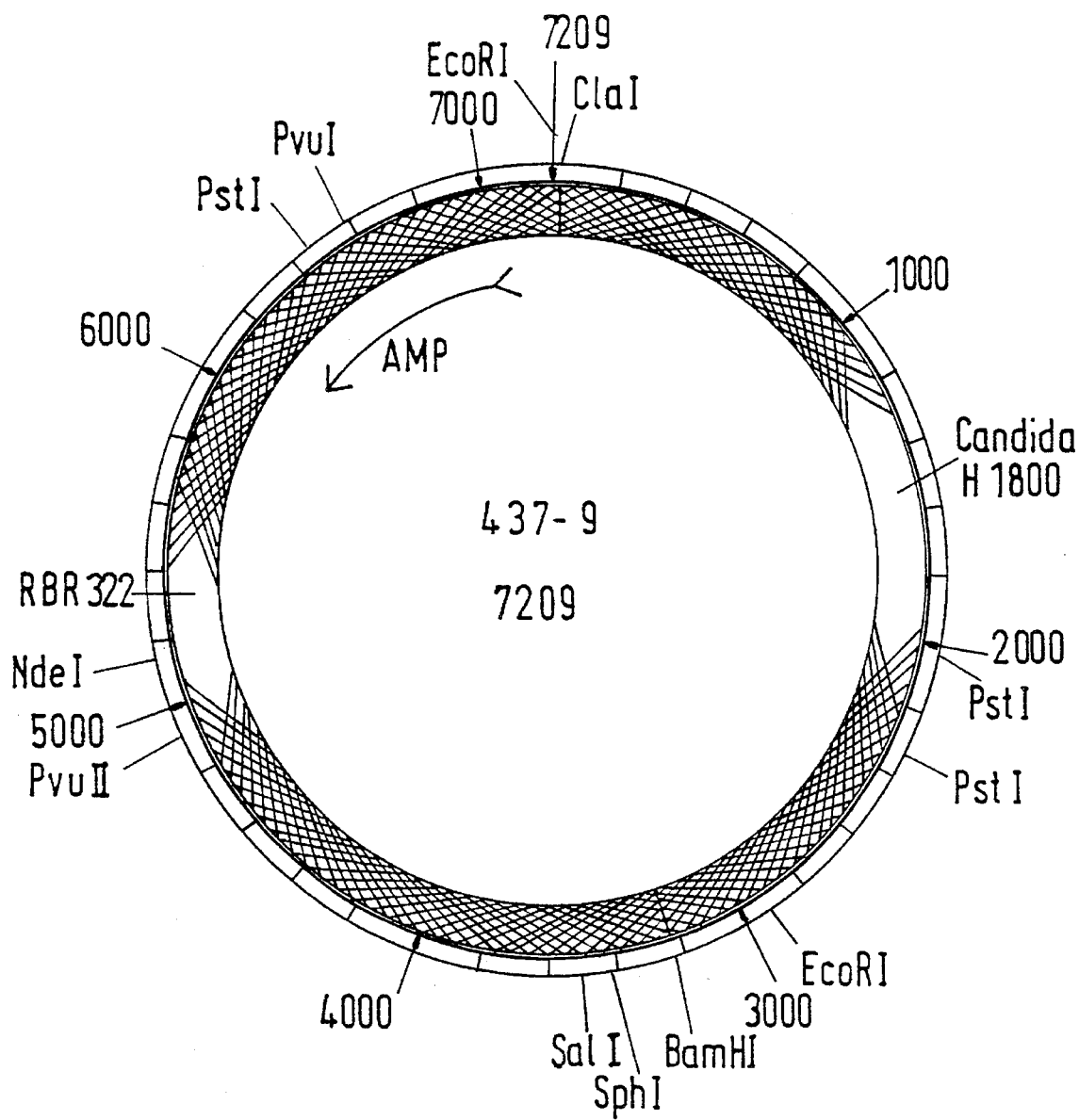

FIG. 6: Restriction map of the 3.2 kb ClaI-BamHI gene-probe fragment 437-3 cloned into the plasmid vector pBR 322.1. Further restriction enzymes which do/do not cut the gene probe are listed in the text.

The gene probe originates from the strain C. albicans H 1800.

TABLE 1

| Strain | Hybridisation with gene probes | | | | | | |
|---|---|---|---|---|---|---|---|
| | 430.14 | 431.19 | 309.06 | 432.8 | 437.3 | 436.1 | 431.19 + 436.1 |
| C. albicans (Ruck) | + | + | + | (+) | − | − | + |
| C. albicans (Hantschke) | + | + | + | − | − | − | + |
| C. albicans ATCC 10231 | + | + | + | (+) | − | − | + |
| C. albicans H 1800 | + | + | + | + | + | + | + |
| C. Krusei | − | − | − | − | − | − | − |
| C. pseudotropicalis | − | − | − | − | − | − | − |
| T. glabrata | − | − | − | − | − | − | − |
| S. cerevisiae | − | − | − | − | − | − | − |
| C. parapsilosis | − | − | − | − | − | − | − |
| C. guilliermondii | − | − | − | − | − | − | − |
| T. candida | − | − | − | − | − | − | − |
| C. tropicalis | − | − | − | − | − | − | − |
| E. coli K12 | − | − | − | − | − | − | − |
| B. subtilis | − | − | − | − | − | − | − |
| Ps. putida | − | − | − | − | − | − | − |
| Ps. aeruginosa | − | − | − | − | − | − | − |
| Staphylococcus aureus | − | − | − | − | − | − | − |
| Aspergillus flavus | − | − | − | − | − | − | − |
| Aspergillus fumigatus | − | − | − | − | − | − | − |
| Aspergillus niger | − | − | − | − | − | − | − |
| Cryptococcus neoformans | − | − | − | − | − | − | − |
| Penicillium chrysogenum | − | − | − | − | − | − | − |
| Penicillium notatum | − | − | − | − | − | − | − |
| Trichophyton rubrum | − | − | − | − | − | − | − |
| Hela 76 | − | − | − | − | − | − | − |
| Vero 177 | − | − | − | − | − | − | − |
| HT20 T-lymphocytes | − | − | − | − | − | − | − |

TABLE 1-continued

| | Hybridisation with gene probes | | | | | | |
|---|---|---|---|---|---|---|---|
| Strain | 430.14 | 431.19 | 309.06 | 432.8 | 437.3 | 436.1 | 431.19 + 436.1 |
| U937 T-lymphocytes | − | − | − | − | − | − | − |

TABLE 2

| | Hybridisation with gene probes | | |
|---|---|---|---|
| Strain | 431.19 | 436.1 | 436.1 + 431.19 |
| *C. albicans* | | | |
| I | + | − | + |
| K1 | + | − | + |
| P6 | + | − | + |
| W | + | − | + |
| 2720/89 | + | − | + |
| 2831/89 | + | − | + |
| 3236/89 | + | − | + |
| 45/90 | + | − | + |
| 1428/90 | + | − | + |
| 2560/90 | + | − | + |
| 1454/91 | + | − | + |
| 1458/91 | + | − | + |
| 1484/91 | + | − | + |
| 1486/91 | + | − | + |
| 1632/91 | + | − | + |
| P8 | + | − | + |
| 1729/91 | + | − | + |
| 1738/91 | + | − | + |
| 1842/91 | + | − | + |
| 1900/91 | + | − | + |
| 1920/91 | + | − | + |
| 1958/91 | + | − | + |
| 1976/91 | + | − | + |
| 1985/91 | + | − | + |
| 1988/91 | + | − | + |
| 2004/91 | + | − | + |
| 2033/91 | + | − | + |
| 2029/91 | + | − | + |
| 2046/91 | + | − | + |
| 2053/91 | + | − | + |
| 2061/91 | + | − | + |
| 2077/91 | + | − | + |
| 2089/91 | + | − | + |
| 2770/91 | + | − | + |
| 3761/91 | + | − | + |
| 3823/91 | + | − | + |
| H1573 | + | − | + |
| H1614 | + | − | + |
| H1667 | + | − | + |
| H1697 | + | − | + |
| H1711 | + | − | + |
| H1726 | + | − | + |
| H1787 | + | − | + |
| H1788 | + | − | + |
| H1790 | + | − | + |
| H1800 | − | + | + |
| H1807 | + | − | + |
| H1808 | + | − | + |
| H1809 | + | − | + |
| H1810 | + | − | + |
| H1811 | + | − | + |
| H1824 | + | − | + |
| H1825 | + | − | + |
| H1826 | + | − | + |
| H1841 | + | − | + |
| H1842 | + | − | + |
| H1843 | + | − | + |
| H1844 | + | − | + |
| H1856b | + | − | + |
| H1857a | + | − | + |
| H1858 | + | − | + |
| H1867 | + | − | + |

TABLE 2-continued

| | Hybridisation with gene probes | | |
|---|---|---|---|
| Strain | 431.19 | 436.1 | 436.1 + 431.19 |
| H1869 | + | − | + |
| H1893a | + | − | + |
| H1893b | + | − | + |
| H1896 | − | + | + |
| H1903 | + | − | + |
| H1905 | − | + | + |
| H1907 | + | − | + |
| H1908 | + | − | + |
| H1910 | + | − | + |
| H1911 | + | − | + |
| H1912 | − | + | + |
| H1923 | + | − | + |
| H1935 | + | − | + |
| H1936 | + | − | + |
| H1973 | + | − | + |
| H1974 | + | − | + |
| H1980 | + | − | + |
| H1990 | + | − | + |
| H1997 | + | − | + |
| H1999 | + | − | + |
| H2006a | + | − | + |

TABLE 3

| Strain | Hybridisation with oligonucleotide probes | | | | | | | | | | |
|---|---|---|---|---|---|---|---|---|---|---|
| | 2 | 3 | 4 | 5 | 6 | 25 | 26 | 27 | 2 + 25 | 4 + 26 | 6 + 27 |
| *C. albicans* (Ruck) | + | + | + | + | + | − | − | − | + | + | + |
| *C. albicans* (Hantschke) | + | + | + | + | + | − | − | − | + | + | + |
| *C. albicans* ATCC 10231 | + | + | + | + | + | − | − | − | + | + | + |
| *C. albicans* H1800 | − | − | − | − | − | + | + | + | + | + | + |
| *C. krusei* | − | − | − | − | − | − | − | − | − | − | − |
| *C. pseudotropicalis* | − | − | − | − | − | − | − | − | − | − | − |
| *T. glabrata* | − | − | − | − | − | − | − | − | − | − | − |
| *S. cerevisiae* | − | − | − | − | − | − | − | − | − | − | − |
| *C. parapsilosis* | − | − | − | − | − | − | − | − | − | − | − |
| *C. guilliermondii* | − | − | − | − | − | − | − | − | − | − | − |
| *T. candida* | − | − | − | − | − | − | − | − | − | − | − |
| *C. tropicalis* | − | − | − | − | − | − | − | − | − | − | − |
| *E. coli* K12 | − | − | − | − | − | − | − | − | − | − | − |
| *B. subtilis* | − | − | − | − | − | − | − | − | − | − | − |
| *Ps. putida* | − | − | − | − | − | − | − | − | − | − | − |
| *Ps. aeruginosa* | − | − | − | − | − | − | − | − | − | − | − |
| *Staphylococcus aureus* | − | − | − | − | − | − | − | − | − | − | − |
| *Aspergillus flavus* | − | − | − | − | − | − | − | − | − | − | − |
| *Aspergillus fumigatus* | − | − | − | − | − | − | − | − | − | − | − |
| *Aspergillus niger* | − | − | − | − | − | − | − | − | − | − | − |
| *Cryptococcus neoformans* | − | − | − | − | − | − | − | − | − | − | − |
| *Penicillium chrysogenum* | − | − | − | − | − | − | − | − | − | − | − |
| *Penicillium notatum* | − | − | − | − | − | − | − | − | − | − | − |
| *Trichophytonrubrum* | − | − | − | − | − | − | − | − | − | − | − |
| Hela 76 | − | − | − | − | − | − | − | − | − | − | − |
| Vero 177 | − | − | − | − | − | − | − | − | − | − | − |
| HT20 T-lymphocytes | − | − | − | − | − | − | − | − | − | − | − |
| U937 T-lymphocytes | − | − | − | − | − | − | − | − | − | − | − | see sequence listing SEQ ID NO: 2–6 and SEQ ID NO: 25–27

---

We claim:

1. DNA consisting of a nucleotide sequence selected from the group consisting of:
   (i) the nucleotide sequence of SEQ ID NO: 1;
   (ii) a nucleotide sequence fully complementary to (i);
   (iii) the nucleotide sequence of a restriction enzyme digestion fragment of (i) or (ii), said restriction enzyme digestion fragment being specific for *Candida albicans;* and
   (iii) the nucleotide sequence of a 100 mer continuous nucleotide fragment of (i) or (ii), said 100 mer continuous nucleotide fragment being specific for *Candida albicans.*

2. DNA according to claim 1, consisting of the nucleotide sequence of SEQ ID NO: 1 or a nucleotide sequence fully complementary thereto.

3. DNA according to claim 1, consisting of a nucleotide sequence of a restriction enzyme digestion fragment of SEQ ID NO: 1 or a nucleotide sequence fully complementary thereto.

4. DNA according to claim 3, wherein said digestion fragment is obtained using a restriction enzyme selected from the group consisting of ClaI, BamHI, SalI, AccI and SphI.

5. DNA according to claim 1, consisting of the nucleotide sequence of a 100 mer continuous nucleotide fragment of SEQ ID NO: 1 or a nudeotide sequence fully complementary thereto.

6. DNA according to claim 5, consisting of a nucleotide sequence selected from the group consisting of SEQ ID NOS: 2–24.

7. DNA consisting of:
   (i) the 2.6 kb ClaI digestion fragment of plasmid 436-1;
   (ii) DNA fully complementary to (i); and
   (iii) DNA consisting of a nucleotide sequence selected from the group consisting of SEQ ID NOS: 25–38.

8. A gene probe consisting of a label and DNA according to claim 1.

9. A gene probe according to claim 8, wherein said DNA consists of the nucleotide sequence of SEQ ID NO: 1 or a nucleotide sequence fully complementary thereto.

10. A gene probe according to claim 8, wherein said DNA consists of a nucleotide sequence of a restriction enzyme digestion fragment of SEQ ID NO: 1 or a nucleotide sequence fully complementary thereto.

11. A gene probe according to claim 10, wherein said restriction enzyme is selected from the group consisting of ClaI, BamHI, SalI, AccI and SphI.

12. A gene probe according to claim 8, wherein said DNA consists of the nucleotide sequence of a 100 mer continuous nucleotide fragment of SEQ ID NO: 1 or a nucleotide sequence fully complementary thereto.

13. A gene probe according to claim 12, wherein said DNA consists of a nucleotide sequence selected from the group consisting of SEQ ID NOS: 2–24.

14. A gene probe consisting of a label and DNA according to claim 7.

15. A method of detecting the presence of *Candida albicans* in a clinical sample comprising:

(i) isolating total DNA from said sample;

(ii) combining said total DNA with a gene probe containing a label and a nucleotide sequence specific for *Candida albicans* under stringent conditions so that said gene probe hybridizes specifically to DNA which may be present from *Candida albicans;* and (iii) detecting the label to give an indication of the presence of *Candida albicans* in said clinical sample; wherein said gene probe is the gene probe according to claim 8.

16. The method according to claim 15, wherein before, after or during step (ii) said total DNA is also combined with a gene probe consisting of a label and DNA having a nucleotide sequence selected from the group consisting of SEQ ID NOS: 25–38.

17. The method according to claim 15 or 16, further comprising amplifying DNA contained in the sample.

18. A method of detecting the presence of *Candida albicans* in a clinical sample comprising:

(i) isolating total DNA from said sample;

(ii) combining said total DNA with a gene probe containing a label and a nucleotide sequence specific for *Candida albicans* under stringent conditions so that said gene probe hybridizes specifically to DNA which may be present from *Candida albicans;* and (iii) detecting the label to give an indication of the presence of *Candida albicans* in said clinical sample; wherein said gene probe is the gene probe according to claim 14.

19. The method according to claim 18, further comprising amplifying DNA contained in the sample.

20. DNA consisting of a nucleotide sequence selected from the group consisting of SEQ ID NOS: 39–44.

21. A reagent composition for detecting *Candida albicans* comprising:

(i) the gene probe of claim 8; and (ii) a gene probe consisting of a label and DNA consisting of a nucleotide sequence selected from the group consisting of SEQ ID NOS: 25–38.

22. A method of detecting the presence of *Candida albicans* in a clinical sample comprising:

(i) isolating total DNA from said sample;

(ii) combining said total DNA with a first gene probe containing a label and a nucleotide sequence specific for *Candida albicans* under stringent conditions so that said gene probe hybridizes specifically to DNA which may be present from *Candida albicans;*

(iii) combining said total DNA with a second gene probe containing a label and a nucleotide sequence specific for *Candida albicans* under stringent conditions so that said gene probe hybridizes specifically to DNA which may be present from *Candida albicans;* and (iv) detecting either label to give an indication of the presence of *Candida albicans* in said clinical sample; wherein steps (ii) and (iii) are carried out in any order or simultaneously;

wherein said nucleotide sequence of said first gene probe which is specific for *Candida albicans* consists of a *Candida albicans*-specific 10 mer to 100 mer continuous fragment of SEQ ID NO: 1 or a nucleotide sequence fully complementary thereto; and wherein said nucleotide sequence of said second gene probe which is specific for *Candida albicans* consists of a *Candida albicans*-specific 10 mer to 100 mer continuous fragment of the 2.6 kb ClaI digestion fragment of plasmid 436-1 or DNA fully complementary thereto.

* * * * *

UNITED STATES PATENT AND TRADEMARK OFFICE
CERTIFICATE OF CORRECTION

PATENT NO.   : 5,489,513
DATED        : February 6, 1996
INVENTOR(S)  : Springer, et al.

It is certified that error appears in the above-indentified patent and that said Letters Patent is hereby corrected as shown below:

Col. 4, line 34    After " techniques. " insert -- The gene probe 436-1 is contained in <u>Escherichia coli</u> strain K 12, 436-1, a sample of which was deposited with the DSM-Deutsche Sammlung von Mikroorganism und Zellkulturen, GmbH, Mascheroder Weg 1b, D-38124, Braunschweig, Germany, on November 10, 1995, under Accession No. DSM 10036. --

Signed and Sealed this

Third Day of September, 1996

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,489,513
DATED : February 6, 1996
INVENTOR(S) : Springer, et al.

It is certified that error appears in the above-indentified patent and that said Letters Patent is hereby corrected as shown below:

Col. 44, claim 5 line 3     Delete " nudeotide " and substitute -- nucleotide --

Signed and Sealed this

Twenty-sixth Day of November 1996

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 44

( 2 ) INFORMATION FOR SEQ ID NO: 1:

( i ) SEQUENCE CHARACTERISTICS:
        ( A ) LENGTH: 2233 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 1:

```
ATCGATGGTA  TCGTCGATGG  TATCGTCGTT  CTGCATGTCG  TTGATGTCAA      50

AGCCAATAAA  GTCGTCAAAG  TTGTCAAACT  TTTGTGGGAC  GGCCTCCTCT     100

GCCTTCTTGG  CCTCCTCTGC  CTTCTTCTTG  GCCTCCTCTG  CCTTCTTCTT     150

GGCCTCCTCT  GCCTTCTTCT  TGGCCTCCTC  TGCCTTCTTC  TTGGCCTCCT     200

CTGCCTTCTT  CTTGGCCTCC  TCTGCCTTCT  TCTTGGCCTC  TTCTTCCTTC     250

TTCTTGGCCT  CTTCTTCCTT  CTTCTTGGCC  TCTTCTTCCT  TCTTCTTAGC     300

CTCTTCTTCA  CGTTTCTTTC  TTGCCGCTGC  TTCTATGACT  TTCAATTCGT     350

CAAATTTCTT  TTTCTTTTCA  ACCATAACGC  CGAGACACCA  CTCTGCATCA     400
```

| | | | | | |
|---|---|---|---|---|---|
| TTGAGTTTCG | ACACTGTTTG | TCTAGAATAG | CATGGAAGTT | TTGGATTTCA | 450 |
| CCGTTGAGCA | GTTGGGTTAT | GGATTTTTGG | ATTAGTTCGT | TGTTGGGGCT | 500 |
| AGTTATCACA | TTGATTTGTT | TTCTGTTTTG | GTCAATTATC | TCAAATATGT | 550 |
| ATCCTGATGA | TTTCAATATC | TCGTCGAGTG | AGTTATGTAA | TCTTGTTTGG | 600 |
| AGGTTTTCTG | GCATGGTGGG | GGGAAATAAA | GGTGTGATAA | AATTATTCTT | 650 |
| GTTGGTTTAT | GCGACGATTG | TGTCAGGGAA | ATAACTCCTT | GATATATGTT | 700 |
| AATATATAGG | GACATCTACA | CCCAGAGTGT | AGACGGAGAC | ACGACCTCCG | 750 |
| AAGGATCGGT | CTGTATAAGG | ACCTGGATGT | GACCTAGACG | AGCTGGTCAA | 800 |
| TCCCGAGGAA | TTGACGAAGT | ATATATCTAC | ATACGCACAC | ATAGTGATTA | 850 |
| ATATACTATT | AAATGTTCAC | TGATACTCAG | ATTCCATTAA | TATAAGTCGT | 900 |
| ACGTATTAGG | TCAACATTGG | TGAAGAATTT | GCACTCATCA | AGAGTCAGGA | 950 |
| ATTAGTATAA | AAAGAAGAGA | AAACAAAGGT | ATTTAGGATA | TAGAGACCGA | 1000 |
| GTTTCAGGAT | GGGGGCTATT | TTTACAACAA | AGTGACGTGA | AAAGGTCAAT | 1050 |
| AGCCACGACT | TGCAGACTCT | TATGCGCAAT | TATGCAAGTT | GTTGCCTTTT | 1100 |
| GTTTACATTT | TTTTGTTTAC | ATTTTTTGTC | GACCTAAGCA | ACATTCATCC | 1150 |
| CTTGCCCGGC | CCCCTATTTT | CACCACCATA | AATGCCATGC | TGGCGTGACC | 1200 |
| TCAAAAATTT | TACTATCCCT | ATCACTTTCT | TTTCCTTCTT | TTTTCACCAT | 1250 |
| TCGTTCATCA | ATCCATTAGT | TTTCATCATA | GATCGACTGA | ATAAGTGCTA | 1300 |
| CTACTTCGAC | TACTGATCCT | TTAAGTTATG | GCAAGTATGA | ATAATACAAC | 1350 |
| TTTTTTGAAG | AATTTGTTT | ACTAACTAAG | TATTATAGAA | AAGTCAGAGA | 1400 |
| TTATTGTTCA | TGATTGTATC | GGTTTCATC | ATAAATCATT | GAAAGATTC | 1450 |
| TAGTCAAGTG | TTTCAGAGAT | GCCCTAAGTT | AAGATATGTA | TGATCATTAC | 1500 |
| CTATGGTTTT | GAAGAATTTT | GTTACTAAC | TAACTAATAT | AGATAATTTA | 1550 |
| TTGATTATTG | TTTGGAGACT | ACCCATAATG | CTTCTGGTAT | CGCGGTTCGG | 1600 |
| TCAGCTATAA | TGATTACACA | ATAGGGTACT | TCTATTTGAC | AACTTCTGTC | 1650 |
| ACATGTTATT | GCTTGATTTG | GCTTGTTCTA | AAGTGTTTTT | TTTTACTGGA | 1700 |
| AATTGATTAT | TCAGGGGTTT | GTAATTGACC | ATAAAATCTA | CATTAAAGTT | 1750 |
| GGCCAAATGG | ACTATCTGAC | TTGCTTTGAT | AAGAGATGAC | AGGATTTTAA | 1800 |
| GGATATCAAC | CTAGTTTTCG | GTGAATTTAT | GGTATCAATT | GAACTTGTGG | 1850 |
| TCCGTGACAA | GGATTACTGA | TAGATAAACC | GTTTTTGCAA | GGTACATTTA | 1900 |
| CCAGTCAACT | AGGATTTATG | ATTCAATATC | AAAAACAGAA | ACCAATTATC | 1950 |
| ACAATGTAGG | TTCTAATATA | TAGTGGTTGT | GTATACACCA | AGAAGTTAAT | 2000 |
| GATTTGTTCA | TAATTAGTGT | GACAGACTAC | ATGAAGTATA | CTATGACTTC | 2050 |
| TCTTGATCAG | TGAAACGCGC | GATTGTTATT | GATTTAATA | TAAAAACGCC | 2100 |
| ACTTTAAATA | CATTTAAAAA | AATGTAAACA | AAACTTTTAA | AACAGTTGAA | 2150 |
| ACACTGAAAT | CAATATAACC | AATGCCTAAC | ACCAACGAAT | TTGAAGACTC | 2200 |
| ATCTCAGCAA | TCTAGAGACA | AACTTTTGGA | TCC | | 2233 |

( 2 ) INFORMATION FOR SEQ ID NO: 2:

( i ) SEQUENCE CHARACTERISTICS:
( A ) LENGTH: 100 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Candida albicans (xi) SEQUENCE DESCRIPTION: SEQ ID NO: 2:

| | | | | | |
|---|---|---|---|---|---|
| ATCGATGGTA | TCGTCGATGG | TATCGTCGTT | CTGCATGTCG | TTGATGTCAA | 50 |
| AGCCAATAAA | GTCGTCAAAG | TTGTCAAACT | TTTGTGGGAC | GGCCTCCTCT | 100 |

(2) INFORMATION FOR SEQ ID NO: 3:

(i) SEQUENCE CHARACTERISTICS:
(A) LENGTH: 100 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Candida albicans (xi) SEQUENCE DESCRIPTION: SEQ ID NO: 3:

| | | | | | |
|---|---|---|---|---|---|
| GCCTTCTTGG | CCTCCTCTGC | CTTCTTCTTG | GCCTCCTCTG | CCTTCTTCTT | 50 |
| GGCCTCCTCT | GCCTTCTTCT | TGGCCTCCTC | TGCCTTCTTC | TTGGCCTCCT | 100 |

(2) INFORMATION FOR SEQ ID NO: 4:

(i) SEQUENCE CHARACTERISTICS:
(A) LENGTH: 100 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Candida albicans (xi) SEQUENCE DESCRIPTION: SEQ ID NO: 4:

| | | | | | |
|---|---|---|---|---|---|
| CTGCCTTCTT | CTTGGCCTCC | TCTGCCTTCT | TCTTGGCCTC | TTCTTCCTTC | 50 |
| TTCTTGGCCT | CTTCTTCCTT | CTTCTTGGCC | TCTTCTTCCT | TCTTCTTAGC | 100 |

(2) INFORMATION FOR SEQ ID NO: 5:

(i) SEQUENCE CHARACTERISTICS:
(A) LENGTH: 100 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO ( i i i ) ANTI-SENSE: NO ( v i ) ORIGINAL SOURCE:
    ( A ) ORGANISM: Candida albicans ( x i ) SEQUENCE DESCRIPTION: SEQ ID NO: 5:

| CTCTTCTTCA | CGTTTCTTTC | TTGCCGCTGC | TTCTATGACT | TTCAATTCGT | 50 |
| CAAATTTCTT | TTTCTTTTCA | ACCATAACGC | CGAGACACCA | CTCTGCATCA | 100 |

( 2 ) INFORMATION FOR SEQ ID NO: 6:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 6:

| TTGAGTTTCG | ACACTGTTTG | TCTAGAATAG | CATGGAAGTT | TTGGATTTCA | 50 |
| CCGTTGAGCA | GTTGGGTTAT | GGATTTTTGG | ATTAGTTCGT | TGTTGGGGCT | 100 |

( 2 ) INFORMATION FOR SEQ ID NO: 7:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 7:

| AGTTATCACA | TTGATTTGTT | TTCTGTTTTG | GTCAATTATC | TCAAATATGT | 50 |
| ATCCTGATGA | TTTCAATATC | TCGTCGAGTG | AGTTATGTAA | TCTTGTTTGG | 100 |

( 2 ) INFORMATION FOR SEQ ID NO: 8:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 8:

| AGGTTTTCTG | GCATGGTGGG | GGGAAATAAA | GGTGTGATAA | AATTATTCTT | 50 |

GTTGGTTTAT GCGACGATTG TGTCAGGGAA ATAACTCCTT GATATATGTT        100

( 2 ) INFORMATION FOR SEQ ID NO: 9:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 9:

AATATATAGG GACATCTACA CCCAGAGTGT AGACGGAGAC ACGACCTCCG        50

AAGGATCGGT CTGTATAAGG ACCTGGATGT GACCTAGACG AGCTGGTCAA        100

( 2 ) INFORMATION FOR SEQ ID NO: 10:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 10:

TCCCGAGGAA TTGACGAAGT ATATATCTAC ATACGCACAC ATAGTGATTA        50

ATATACTATT AAATGTTCAC TGATACTCAG ATTCCATTAA TATAAGTCGT        100

( 2 ) INFORMATION FOR SEQ ID NO: 11:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 11:

ACGTATTAGG TCAACATTGG TGAAGAATTT GCACTCATCA AGAGTCAGGA        50

ATTAGTATAA AAAGAAGAGA AAACAAAGGT ATTTAGGATA TAGAGACCGA        100

( 2 ) INFORMATION FOR SEQ ID NO: 12:

( i ) SEQUENCE CHARACTERISTICS:
        ( A ) LENGTH: 100 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Candida albicans (xi) SEQUENCE DESCRIPTION: SEQ ID NO: 12:

```
GTTTCAGGAT GGGGGCTATT TTTACAACAA AGTGACGTGA AAAGGTCAAT        50
AGCCACGACT TGCAGACTCT TATGCGCAAT TATGCAAGTT GTTGCCTTTT       100
```

(2) INFORMATION FOR SEQ ID NO: 13:

(i) SEQUENCE CHARACTERISTICS:
(A) LENGTH: 100 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Candida albicans (xi) SEQUENCE DESCRIPTION: SEQ ID NO: 13:

```
GTTTACATTT TTTTGTTTAC ATTTTTTGTC GACCTAAGCA ACATTCATCC        50
CTTGCCCGGC CCCCTATTTT CACCACCATA AATGCCATGC TGGCGTGACC       100
```

(2) INFORMATION FOR SEQ ID NO: 14:

(i) SEQUENCE CHARACTERISTICS:
(A) LENGTH: 100 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Candida albicans (xi) SEQUENCE DESCRIPTION: SEQ ID NO: 14:

```
TCAAAAATTT TACTATCCCT ATCACTTTCT TTTCCTTCTT TTTTCACCAT        50
TCGTTCATCA ATCCATTAGT TTTCATCATA GATCGACTGA ATAAGTGCTA       100
```

(2) INFORMATION FOR SEQ ID NO: 15:

(i) SEQUENCE CHARACTERISTICS:
(A) LENGTH: 100 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO 5,489,513

27

-continued

28

( i i i ) ANTI-SENSE: NO ( v i ) ORIGINAL SOURCE:
               ( A ) ORGANISM: Candida albicans ( x i ) SEQUENCE DESCRIPTION: SEQ ID NO: 15:

| CTACTTCGAC | TACTGATCCT | TTAAGTTATG | GCAAGTATGA | ATAATACAAC | 50  |
| TTTTTGAAG  | AATTTTGTTT | ACTAACTAAG | TATTATAGAA | AAGTCAGAGA | 100 |

( 2 ) INFORMATION FOR SEQ ID NO: 16:

( i ) SEQUENCE CHARACTERISTICS:
               ( A ) LENGTH: 100 base pairs
               ( B ) TYPE: nucleic acid
               ( C ) STRANDEDNESS: single
               ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
               ( A ) ORGANISM: Candida albicans ( x i ) SEQUENCE DESCRIPTION: SEQ ID NO: 16:

| TTATTGTTCA | TGATTGTATC | GGTTTTCATC | ATAAATCATT | GAAAAGATTC | 50  |
| TAGTCAAGTG | TTTCAGAGAT | GCCCTAAGTT | AAGATATGTA | TGATCATTAC | 100 |

( 2 ) INFORMATION FOR SEQ ID NO: 17:

( i ) SEQUENCE CHARACTERISTICS:
               ( A ) LENGTH: 100 base pairs
               ( B ) TYPE: nucleic acid
               ( C ) STRANDEDNESS: single
               ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
               ( A ) ORGANISM: Candida albicans ( x i ) SEQUENCE DESCRIPTION: SEQ ID NO: 17:

| CTATGGTTTT | GAAGAATTTT | GTTTACTAAC | TAACTAATAT | AGATAATTTA | 50  |
| TTGATTATTG | TTTGGAGACT | ACCCATAATG | CTTCTGGTAT | CGCGGTTCGG | 100 |

( 2 ) INFORMATION FOR SEQ ID NO: 18:

( i ) SEQUENCE CHARACTERISTICS:
               ( A ) LENGTH: 100 base pairs
               ( B ) TYPE: nucleic acid
               ( C ) STRANDEDNESS: single
               ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
               ( A ) ORGANISM: Candida albicans ( x i ) SEQUENCE DESCRIPTION: SEQ ID NO: 18:

| TCAGCTATAA | TGATTACACA | ATAGGGTACT | TCTATTTGAC | AACTTCTGTC | 50 |

ACATGTTATT GCTTGATTTG GCTTGTTCTA AAGTGTTTTT TTTTACTGGA          100

( 2 ) INFORMATION FOR SEQ ID NO: 19:

( i ) SEQUENCE CHARACTERISTICS:
  ( A ) LENGTH: 100 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
  ( A ) ORGANISM: Candida albicans ( x i ) SEQUENCE DESCRIPTION: SEQ ID NO: 19:

AATTGATTAT TCAGGGGTTT GTAATTGACC ATAAAATCTA ACATTAAAGT          50

GGCCAAATGG ACTATCTGAC TTGCTTTGAT AAGAGATGAC AGGATTTTAA          100

( 2 ) INFORMATION FOR SEQ ID NO: 20:

( i ) SEQUENCE CHARACTERISTICS:
  ( A ) LENGTH: 100 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
  ( A ) ORGANISM: Candida albicans ( x i ) SEQUENCE DESCRIPTION: SEQ ID NO: 20:

GGATATCAAC CTAGTTTTCG GTGAATTTAT GGTATCAATT GAACTTGTGG          50

TCCGTGACAA GGATTACTGA TAGATAAACC GTTTTTGCAA GGTACATTTA          100

( 2 ) INFORMATION FOR SEQ ID NO: 21:

( i ) SEQUENCE CHARACTERISTICS:
  ( A ) LENGTH: 100 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
  ( A ) ORGANISM: Candida albicans ( x i ) SEQUENCE DESCRIPTION: SEQ ID NO: 21:

CCAGTCAACT AGGATTTATG ATTCAATATC AAAAACAGAA ACCAATTATC          50

ACAATGTAGG TTCTAATATA TAGTGGTTGT GTATACACCA AGAAGTTAAT          100

( 2 ) INFORMATION FOR SEQ ID NO: 22:

( i ) SEQUENCE CHARACTERISTICS:
  ( A ) LENGTH: 100 base pairs ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 22:

| | | | | | |
|---|---|---|---|---|---|
| GATTTGTTCA | TAATTAGTGT | GACAGACTAC | ATGAAGTATA | CTATGACTTC | 50 |
| TCTTGATCAG | TGAAACGCGC | GATTGTTATT | GATTTAATA | TAAAAACGCC | 100 |

( 2 ) INFORMATION FOR SEQ ID NO: 23:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 23:

| | | | | | |
|---|---|---|---|---|---|
| ACTTTAAATA | CATTTAAAAA | AATGTAAACA | AAACTTTTAA | AACAGTTGAA | 50 |
| ACACTGAAAT | CAATATAACC | AATGCCTAAC | ACCAACGAAT | TTGAAGACTC | 100 |

( 2 ) INFORMATION FOR SEQ ID NO: 24:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 24:

| | | | |
|---|---|---|---|
| ATCTCAGCAA | TCTAGAGACA | AACTTTTGGA | TCC | 33 |

( 2 ) INFORMATION FOR SEQ ID NO: 25:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
    ( A ) ORGANISM: Candida albicans ( x i ) SEQUENCE DESCRIPTION: SEQ ID NO: 25:

| | | | | | |
|---|---|---|---|---|---|
| ATCGATTGAT | TTTCAATTTC | TTATTGTTTG | AATGATGTGG | CTCAACAAAA | 50 |
| TGAAAATGGA | GAAACACCAT | AAAACACGGT | AGAAGTTGCC | AATTTTGTTT | 100 |

( 2 ) INFORMATION FOR SEQ ID NO: 26:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 26:

| | | | | | |
|---|---|---|---|---|---|
| AAGAATAAAT | CCACCAATAT | ATATACACAA | AGTTCTTACG | AATGTTTGTG | 50 |
| TTATGATTTT | GAGCCCACAA | GGACTTTGCA | GAGGATTATT | GTTTAATTGG | 100 |

( 2 ) INFORMATION FOR SEQ ID NO: 27:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 27:

| | | | | | |
|---|---|---|---|---|---|
| TTGGCTTGTA | TTCTATGTTG | GAACTGACTT | TTTTTTACTT | TGCTTCTCTT | 50 |
| TATTTGGAAA | CTCCATATAC | CTCGTTGGAA | TATATAAGAA | GTACTAATAT | 100 |

( 2 ) INFORMATION FOR SEQ ID NO: 28:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 28:

| | | | | | |
|---|---|---|---|---|---|
| GTCACTAGAA | AGTATTATAT | TACAACTTGG | AATGTATAAT | AATATCTTCA | 50 |
| AGCAATTCAT | ATCAACAACA | ATTCTTTTGC | TATCAGCATC | ACTGCACCAA | 100 |

( 2 ) INFORMATION FOR SEQ ID NO: 29:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 29:

```
AAAAACAGCC  TTGATAATAA  CAATAATGCA  GATGATGATA  AATATGCAAG        50

AATAAAAGTT  AGTCAATTCT  GGTTATTAAC  GTGAATGAAT  GAATAGATGA       100
```

( 2 ) INFORMATION FOR SEQ ID NO: 30:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 30:

```
AATCTGCAAT  CGTAAGAGTG  TAGGTGAAGG  TGAAATGCAT  AAAAAATTAA        50

CAAATCTGAA  CAATCAACAC  GCCTTTGACC  TCTTTTTTTT  TTTATTATTT       100
```

( 2 ) INFORMATION FOR SEQ ID NO: 31:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 31:

```
CTTGCAACGT  TCTTTTCTAA  TT                                        22
```

( 2 ) INFORMATION FOR SEQ ID NO: 32:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear (ii) MOLECULE TYPE: DNA (genomic)

(iii) HYPOTHETICAL: NO (iii) ANTI-SENSE: NO (vi) ORIGINAL SOURCE:
 (A) ORGANISM: Candida albicans (xi) SEQUENCE DESCRIPTION: SEQ ID NO: 32:

```
TGAACCTGTT GGATTAGTTT GTGTTGTAGT AGTAGTGATT GTTCCTGTCC        50
ATTCACTAGT AACAGTTGTG GTAGTGTGAT ATGGAACATC AACAATAACA       100
```

(2) INFORMATION FOR SEQ ID NO: 33:

(i) SEQUENCE CHARACTERISTICS:
 (A) LENGTH: 100 base pairs
 (B) TYPE: nucleic acid
 (C) STRANDEDNESS: single
 (D) TOPOLOGY: linear (ii) MOLECULE TYPE: DNA (genomic)

(iii) HYPOTHETICAL: NO (iii) ANTI-SENSE: NO (vi) ORIGINAL SOURCE:
 (A) ORGANISM: Candida albicans (xi) SEQUENCE DESCRIPTION: SEQ ID NO: 33:

```
GTAGCAGTTT GTCCTATTGG TACAGTTTGG GTTCTGTAGG AAGTAGTCAC        50
ACCAACATAT GATGTTGTGA TGGTAGTTGT TGGAATGGGT TGCAAAATTT       100
```

(2) INFORMATION FOR SEQ ID NO: 34:

(i) SEQUENCE CHARACTERISTICS:
 (A) LENGTH: 100 base pairs
 (B) TYPE: nucleic acid
 (C) STRANDEDNESS: single
 (D) TOPOLOGY: linear (ii) MOLECULE TYPE: DNA (genomic)

(iii) HYPOTHETICAL: NO (iii) ANTI-SENSE: NO (vi) ORIGINAL SOURCE:
 (A) ORGANISM: Candida albicans (xi) SEQUENCE DESCRIPTION: SEQ ID NO: 34:

```
CAATTGTTTT AGTTTTGTCA ACATCGGAAT TGAATGGTAA AGTAGTCACA        50
GCAGTAGTAC TATCTGTAAC TGTTCTAGTT GTAGCCACAA TGACAATACC       100
```

(2) INFORMATION FOR SEQ ID NO: 35:

(i) SEQUENCE CHARACTERISTICS:
 (A) LENGTH: 100 base pairs
 (B) TYPE: nucleic acid
 (C) STRANDEDNESS: single
 (D) TOPOLOGY: linear (ii) MOLECULE TYPE: DNA (genomic)

(iii) HYPOTHETICAL: NO (iii) ANTI-SENSE: NO (vi) ORIGINAL SOURCE:
 (A) ORGANISM: Candida albicans ( x i ) SEQUENCE DESCRIPTION: SEQ ID NO: 35:

CTTGGAACCA GCTTCACTAT TATTGTATCC GGACCATCTC AAAGTAAATG    50

GATCATCTAT AAAACTGCTA CCAACACAAG TATAATTATT AGCATATGAC    100

( 2 ) INFORMATION FOR SEQ ID NO: 36:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 36:

AAAATATACT GTTTAACATC CGGAGCAGAT ACATAAACGT CAATAAATGG    50

ACGATAACCT GCAGGGATAT TTTCATATGT GATAGAGATA CCATTAGATG    100

( 2 ) INFORMATION FOR SEQ ID NO: 37:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 37:

AACAATTTTT CTTGTAACTA AATGAATCAT ATGATAACGG ATGATCCCAA    50

TCATTCACTC CTTTGAAATC CCAATATGAA CATTTGAACA GTCTATAGTG    100

( 2 ) INFORMATION FOR SEQ ID NO: 38:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Candida albicans ( x i ) SEQUENCE DESCRIPTION: SEQ ID NO: 38:

TATGCGCACC CGTTCTCGGA GCACTGTCCG ACCGCTTTGG CCGCCGCCCA    50

GTCCTGCTTT CGCTACTTGG AGCTCAACTA TCGACTACGC GCTCATGTG    99

( 2 ) INFORMATION FOR SEQ ID NO: 39:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i i i ) ANTI-SENSE: NO ( v i ) ORIGINAL SOURCE:
        ( C ) INDIVIDUAL ISOLATE: primer- DNA ( x i ) SEQUENCE DESCRIPTION: SEQ ID NO: 39:

TCGTCGATGG TATCGTCGTT CTGC     24

( 2 ) INFORMATION FOR SEQ ID NO: 40:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i i i ) ANTI-SENSE: NO ( v i ) ORIGINAL SOURCE:
        ( C ) INDIVIDUAL ISOLATE: primer- DNA ( x i ) SEQUENCE DESCRIPTION: SEQ ID NO: 40:

CCGAACCGCC ATACCAGAAG CATT     24

( 2 ) INFORMATION FOR SEQ ID NO: 41:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i i i ) ANTI-SENSE: NO ( v i ) ORIGINAL SOURCE:
        ( C ) INDIVIDUAL ISOLATE: primer- DNA ( x i ) SEQUENCE DESCRIPTION: SEQ ID NO: 41:

CCGAACCGCG ATACCAGAAG CATT     24

( 2 ) INFORMATION FOR SEQ ID NO: 42:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i i i ) ANTI-SENSE: NO (v i) ORIGINAL SOURCE:
    (C) INDIVIDUAL ISOLATE: primer-DNA (x i) SEQUENCE DESCRIPTION: SEQ ID NO: 42:

TTCTTACGAA TGTTTGTGTT                           20

(2) INFORMATION FOR SEQ ID NO: 43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: YES (i i i) ANTI-SENSE: NO (v i) ORIGINAL SOURCE:
        (C) INDIVIDUAL ISOLATE: primer-DNA (x i) SEQUENCE DESCRIPTION: SEQ ID NO: 43:

ATCCACCAAT ATATATACAC A                         21

(2) INFORMATION FOR SEQ ID NO: 44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: YES (i i i) ANTI-SENSE: NO (v i) ORIGINAL SOURCE:
        (C) INDIVIDUAL ISOLATE: primer-DNA (x i) SEQUENCE DESCRIPTION: SEQ ID NO: 44:

TTTGTCCTAT TGGTACAGTT                           20